United States Patent
Zhu et al.

(10) Patent No.: US 9,646,139 B1
(45) Date of Patent: May 9, 2017

(54) CHEMICAL STRUCTURE-INFORMED METABOLOMICS DATA ANALYSIS

(71) Applicants: Hongjie Zhu, Flemington, NJ (US); Man Luo, Flemington, NJ (US)

(72) Inventors: Hongjie Zhu, Flemington, NJ (US); Man Luo, Flemington, NJ (US)

(*) Notice: Subject to any disclaimer, the term of this patent is extended or adjusted under 35 U.S.C. 154(b) by 174 days.

(21) Appl. No.: 14/564,054

(22) Filed: Dec. 8, 2014

(51) Int. Cl.
*G06F 19/00* (2011.01)

(52) U.S. Cl.
CPC .......... *G06F 19/703* (2013.01); *G06F 19/705* (2013.01); *G06F 19/708* (2013.01)

(58) Field of Classification Search
None
See application file for complete search history.

(56) References Cited

U.S. PATENT DOCUMENTS

| | | | |
|---|---|---|---|
| 7,433,787 B2 | 10/2008 | Barrett | |
| 7,561,975 B2 | 7/2009 | Young | |
| 7,947,453 B2 | 5/2011 | Kaddurah-Daouk | |
| 7,949,475 B2 | 5/2011 | Barrett | |
| 8,026,049 B2 * | 9/2011 | Assadi-Porter | C12Q 1/6883 435/4 |
| 8,175,816 B2 | 5/2012 | Barrett | |
| 2008/0120041 A1 * | 5/2008 | Ridder | G06F 19/702 702/19 |
| 2008/0140370 A1 * | 6/2008 | Kuhlmann | G06F 19/703 703/11 |
| 2009/0065687 A1 * | 3/2009 | Gross | H01J 49/0418 250/281 |
| 2009/0093971 A1 * | 4/2009 | Barrett, Jr. | G06F 19/703 702/22 |
| 2015/0116318 A1 * | 4/2015 | Obrien | G06F 19/26 345/419 |

FOREIGN PATENT DOCUMENTS

AT    EP 2284540 A1 * 2/2011  ......... G01N 33/6893

OTHER PUBLICATIONS

Alexander Korman, Statistical Methods in Metabolomics, Methods in Molecular Biology, 2012, 381-413, 856, Humana Press.
Johan Trygg, Chemometrics Techniques for Metabonomics, The Handbook of Metabonomics and Metabolomics, 2007, 171-199, Elsevier, Amsterdam and Oxford.
Timothy Ebbels, Non-linear Methods for the Analysis of Metabolic Profiles, The Handbook of Metabonomics and Metabolomics, 2007, 201-226, Elsevier, Amsterdam and Oxford.

* cited by examiner

Primary Examiner — Charlie Y Peng

(57) ABSTRACT

This invention relates to statistically significant methods for metabolomics data analysis that incorporate the structure information of metabolites. Understanding of disease pathogenesis and drug effects, as well as prediction of variation in drug response can be achieved by analyzing quantitative data measuring metabolomics biomarker profiles from biological samples. This invention is to boost the statistical power of analyzing metabolomics data. The comprising methods may include retrieving information of metabolites' chemical structures, converting them into structural data, and integrating the structural data into analysis of metabolite concentration data to improve the evaluation of metabolites and to better identify metabolomics signatures.

14 Claims, 5 Drawing Sheets

CHEMICAL STRUCTURE-INFORMED METABOLOMICS DATA ANALYSIS

CROSS-REFERENCE TO RELATED APPLICATIONS

This application claims the benefit of provisional patent application Ser. No. 61/913,368, filed 2013 Dec. 8 by the present inventors.

BACKGROUND OF THE INVENTION

Living organisms are autonomous chemical systems involving numerous molecular entities and chemical processes, such as water, sugars, amino acids, and the processes which translate one into the other. The complexity of life is constituted with numerous biochemical processes involving controlling information flow through biochemical signaling and the flow of chemical energy through metabolism. For example, sugars can be break down through a series of oxidative reactions to small sugar derivatives, providing chemical energy for cells and other basic biological activities, and ultimately to carbon dioxide and water. The intermediates and products of metabolism are called metabolites. Metabolites have various functions, including fuel, structure, signaling, stimulatory and inhibitory effects on enzymes, catalytic activity of their own, defense, and so on. The concentration levels of various metabolites may be related to or directly contribute to various phenotypes of the living organisms, such as disease status and drug response. For example, high glucose is related to diabetes, and high low-density lipoprotein and triglyceride to various cardiovascular diseases.

Over the past decades, major advances in analytical chemistry have resulted in the emergence of the discipline metabolomics. It includes using analytical devices to simultaneous identify and quantify hundreds to thousands of metabolites present in one or a plurality of biological samples, e.g., plasma, urine, and cerebrospinal fluid (CSF). US patents that developed systems and methods to process signals from the analytical devices to identify and quantify metabolites include: U.S. Pat. No. 7,561,975, entitled System, Method, And Computer Program Product For Analyzing Spectrometry Data to Identify and Quantify Individual Components in a Sample; U.S. Pat. No. 7,949,475, entitled System and Method for Analyzing Metabolomic Data; U.S. Pat. No. 8,175,816, entitled System And Method for Analyzing Metabolomic Data; and U.S. Pat. No. 7,433,787, entitled System, Method, and Computer Program Product Using a Database in a Computing System to Compile and Compare Metabolomic Data Obtained from a Plurality of Samples.

The identities and concentration levels of the metabolites, sometimes called "metabotype", usually reflect net interactions between genes and environment, providing information that can possibly bridge a gap between genotype and phenotype. Attesting to this belief, metabolomics has been widely used to understand disease pathogenesis and drug effects, as well as to predict variations in drug response, including both efficacy and safety, among many other applications, which were partially described in U.S. Pat. No. 7,947,453, entitled Methods for Drug Discovery, Disease Treatment, and Diagnosis Using Metabolomics. These applications of metabolomics typically involve identifying "metabolomics signatures" among the metabolites: examples of such metabolomics signatures are 1) metabolites that are influenced by a stimulus, e.g., a drug treatment, and 2) metabolites that are associated with a phenotype of interest, e.g., a disease status or a drug response. These metabolomics signatures can help understand pathologies of different kinds of diseases, identify better targets for drug development, among many other applications.

To achieve the aforementioned goals, metabolomics data needs to be analyzed using some statistical or other analytical methods run on computer processors in communication with a database that stores the metabolomics data along with other necessary data. Common metabolomics data analysis practice uses routine statistical tools, such as Student's t-tests and regression techniques, to identify the metabolomics signatures. These methods, as well as many multivariate chemometrics and statistics tools, including those that were reviewed in Korman et al. (*Methods Mol Biol*, 856: 381-413, 2012) and Lindon et al. (*The Handbook of Metabonomics and Metabolomics.* Elsevier, Amsterdam and Oxford, 2007), essentially treat metabolites as individual variables instead of biological entities, of which, however, some prior knowledge may have been accumulated and is accessible from literatures and/or databases.

Since metabolomics data is usually noisy and the number of samples in metabolomics studies is often limited due to limited budget or other reasons, metabolomics studies often face the so-called "lack-of-power" issue. That is even there exist true metabolomics signatures, a metabolomics data analysis may fail to identify some of them. Therefore, there is a keen need to develop methods to improve the performance of metabolomics data analysis, so that metabolomics can better help improve human health and/or to better facilitate other researches.

Advantages of the Invention

We developed new methods and systems that incorporate chemical structure information of metabolites into metabolomics data analysis to improve its performance. The rational is described in the following paragraph.

As has been known for decades, a distinctive attribute of metabolites is that each of them can be characterized by its unique chemical structure. The structure of metabolites can be quantified, for example, by a variety of structure variables (SV), many of which are also called molecular descriptors (MD) (Todeschini, *Molecular Descriptors for Chemoinformatics*. Wiley, Weinheim, Germany, 2nd edition, 2009). It has been acknowledged that many physico-chemical and/or pharmacological properties of compounds could be revealed by their structure information. For instance, medicinal chemists utilize the structure-activity relationships (SAR) identified from a series of compounds targeting a specific binding protein to design new drugs with better bioactivity (Patani and LaVoie, *Chem Rev.*, 96: 3147-3176, 1996); toxicologists predict a specific toxicity profile of a compound based on its similar key structural moiety with known toxins (Cronin and Dearden, *Quantitative Structure-Activity Relationships*, 14: 329-334, 1995; Nelson, *Biological Reactive Interme-diates Vi*, 500: 33-43, 2001). It has also been observed that the concentration levels of metabolites sharing the same or similar key chemical structures are more likely to be affected together under certain environmental stimulus. For example, serotonin (5-HT) and dopamine (DA) are both monoamine neurotransmitters, structurally similar to each other, but belong to different pathways. Under the stimulus of 3,4-methylenedioxymethamphetamine (MDMA), which interacts with both 5-HT and DA receptors, the level of these two metabolites are both up-regulated in the brain, leading to the hallucinogenic effect (Capela et al., *Mol Neurobiol*, 39: 210-71, 2009). In general, the function and bioactivity of metabolites are closely tied to their structures.

We also showed in practice the advantages of one embodiment of the invention described below over methods for metabolomics data analysis not using structure information. First, we performed extensive "simulations" to compare the performance on identifying metabolomics signatures of the embodiment of the invention to the optimal performance in theory that can be achieved without incorporating structure information. In these simulations, we used a computer to generate metabolomics data and thus know which metabolites are true metabolomics signatures. Results clearly show the embodiment of the invention outperforms the optimum performance that can be achieved without incorporating structure information. Second, we applied the embodiment of the invention to study Alzheimer's disease (AD), seeking new metabolomics signatures for AD. The embodiment of the invention identified that several metabolites on two key neurotransmitter pathways, as well as three carbohydrates and pseudouridine, were elevated in AD patients compared to healthy controls. These AD metabolomics signatures are well supported by existing knowledge on the molecular mechanisms of AD; several of the signatures were not identified by routine methods before. The metabolomics study of AD is also given below for examplification of the embodiment of the invention.

SUMMARY OF THE INVENTION

We developed new systems and methods using a computer to analyze metabolomics data. The metabolomics data includes relative or absolute concentration levels of a plurality of metabolites in a plurality of samples. The systems and methods using a storage medium for storing data and one or a plurality of computer processors for processing data and making calculations comprise: retrieving chemical structures of the metabolites; converting the chemical structures of the metabolites into structure data of the metabolites including a plurality of SVs, each of which takes a certain value for each metabolite; summarizing the SVs into one or a plurality of summary structure variables (SSV); analyzing the relative or absolute concentration levels of the metabolites with or without other input data to derive one or a plurality of original test statistics for the metabolites, which are typically routine analysis results without further incorporating structure information of the metabolites; and integrating the SVs or the SSVs with the original test statistics of the metabolites to derive new test statistics for the metabolites, whereby the structure data of the metabolites is incorporated to improve the evaluation of the metabolites in the metabolomics data. The invented methods and systems may also include evaluating the relevance of the structure data so as to help determine whether the structure data should be included for a particular metabolomics study.

The invented methods and systems can be applied to answer many research questions in typical metabolomics studies. Examples are 1) identifying metabolites that are influenced by an environmental stimulus, e.g., drug treatment, 2) identifying metabolites that are associated with a phenotype of interest, e.g., a disease status, a drug efficacy phenotype, or a drug safety phenotype.

DETAILED DESCRIPTION OF THE FIRST EMBODIMENT

Figure 1:
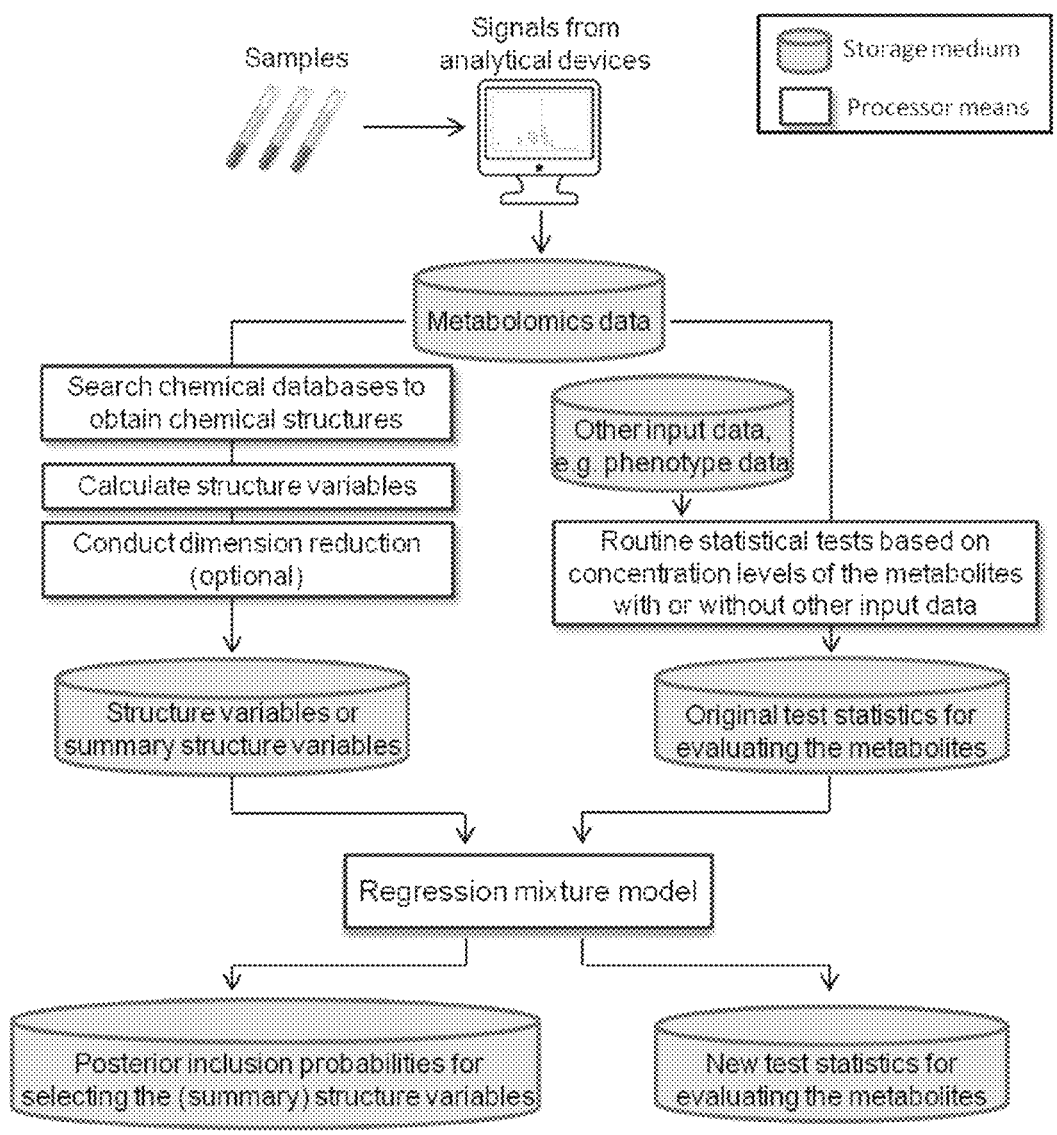
FIG. 1 illustrates the structures of the first embodiment of the invention.

The first embodiment of the invention is illustrated in FIG. 1. Below we provide detailed description of each component of the first embodiment. During the description, we will also mention some variations of each component.

Storage Medium for Storing Data

The embodiment includes storage medium to store all the necessary data to achieve a particular goal or to answer a particular research question of a metabolomics study. Such data may include metabolomics data, i.e., absolute or relative concentration levels of metabolites in a plurality of samples, phenotype data, covariate data, data of sample time, and other necessary data.

Computer Processors in Communication with the Storage Medium for Processing Data and Making Calculations The processors will run pre-programed data processing and calculations.

Retrieving Chemical Structures of the Metabolites

Given the identity of metabolites in a metabolomics dataset, chemical structures of each metabolite can be retrieved by searching on a chemical database. Examples are CAS databases (http://www.cas.org/content/cas-databases), PubChem (https://pubchem.ncbi.nlm.nih.gov/), ChemSpider (http://www.chemspider.com/), KEGG (http://www.genome.jp/kegg/), CHEMBL (https://www.ebi.ac.uk/chembl/), Drug Bank (http://www.drugbank ca/), and CHEBI (http://www.ebi.ac.uk/chebi/). The derived chemical structures are then stored in the aforementioned storage medium.

Converting the Chemical Structures of the Metabolites into Structure Data of the Metabolites There are many methods and software that can be run on computer processors to calculate a wide range of SVs for each metabolite, e.g., ADAPT, ADMET predictor, ADRIANA code, ALMOND, BlueDesc, CDK, CODESSA, CoMFA, Dragon, E-Dragon, GRID, ISIDA, JOELib, MARVIN Beans, MOE, MOLCONN-Z, MOLGEN-QSPR, MOLD2, PaDEL, PowerMV, and PreADMET. The SVs include molecular descriptors (MD), MACCS key fingerprints, Daylight fingerprints, and other topological and three-dimensional fingerprints. The data matrix of all the SVs for the metabolites constitutes structure data, which is then stored in the aforementioned storage medium.

Summarizing the Structure Variables into One or a Plurality of Summary Structure Variables Optionally, one can further summarize the SVs into summary structure variables (SSV) using a dimension reduction method. Example methods are principal component analysis (PCA), variations of PCA, kernel principal component analysis, factor analysis, variations of factor analysis, singular value decomposition, isomap, variations of isomap, multidimensional scaling, and variations of multidimensional scaling. Note that the SSVs can be the original SVs themselves. That is no actual summarization or dimension reduction is performed.

Analyzing the Relative or Absolute Concentration Levels of the Metabolites with or without Other Input Data to Derive One or a Plurality of Original Test Statistics for the Metabolites As mentioned earlier, this invention is applicable to many research questions in typical metabolomics studies, as long as these questions can be also answered by analyzing the relative or absolute concentration levels of the metabolites with or without other input data using some routine statistical tools. One class of such research questions in metabolomics studies are the so-called hypothesis-testing problems. Examples include testing which metabolites are influenced by a drug treatment, or which metabolites are associated with a clinical phenotype.

This step of the first embodiment of the invention involves using the routine statistical tools to analyze metabolomics data with or without other input data to answer a certain research question, and then deriving one or a plurality of original test statistics for each metabolite. For example, suppose paired t-tests are used to answer the question of which metabolites are influenced by a drug treatment, then the original test statistics can be a t-statistic and a p-value for each metabolite. The other input data include all necessary data other than the metabolomics data to answer the research question of interest. For example, suppose linear regressions are used to answer which metabolites are associated with a certain phenotype, then the other input data will include the phenotype data.

Integrating the SVs or the SSVs with the Original Test Statistics of the Metabolites to Derive New Test Statistics for the Metabolites Different statistical methods programmed to run on the computer processors can be used to integrate the SVs or the SSVs with the original test statistics of the metabolites derived in the previous steps to derive new test statistics for the metabolites, so that the structure information of the metabolites can be used to improve the evaluation of the metabolites and thus better answer the research question of interest.

To give examples of such statistical methods, we use the aforementioned hypothesis testing problems as examples. In such problems, each metabolite is assumed to be in either of the following two states: the null hypothesis is true or it is not true (non-null). We refer to them as null and non-null metabolites, respectively. We use an indicator variable $C_i$ to denote the states of metabolites: $C_i=0$ ($C_i=1$) corresponds to that the null (non-null) hypothesis holds for the i-th metabolite. The non-null metabolites are usually the metabolomics signatures to be identified.

Below we describe one of the statistical methods that can be used: the regression mixture (RM) model. The RM model adopts a finite mixture model framework based on a transformation to the original test statistics of metabolites. The specific transformation depends on what routine statistical method is used and what routine test statistics of the metabolites are derived. Suppose a p-value is derived for each metabolite, then a z-score can be calculated for a metabolite i from its p-value, $p_i$: $z_i=\Phi^{-1}(1-p_i)$, where $\Phi$ represents the cumulative standard normal distribution. Then the distribution of the z-scores can be modeled by a two-component RM model:

$$f(z_i)=\pi_{i,0}f_0(z_i)+\pi_{i,1}f_1(z_i), \quad (2)$$

where $\pi_{i,0}$ and $\pi_{i,1}$ are the metabolite-specific prior probabilities for the metabolite i being in different states: $\pi_{i,0}=\Pr(C_i=0)$ and $\pi_{i,1}=\Pr(C_i=1)$, and $f_0$ and $f_1$ are component density functions, which can be normal density or other types of density functions. Note that one can also use more than two components in the model. The prior probabilities are modeled by the SVs or the SSVs through a logit link model:

$$\text{logit}(\pi_{i,1})=\log(\pi_{i,1}/\pi_{i,0})=\beta_0+\Sigma_{j=1}^{d}\beta_j D_{i,j},$$

where D is the design matrix of the SVs or the SSVs with $D_{i,j}$ representing the value of the j-th SV or SSV for the metabolite i, d is the number of the SVs or the SSVs used, and $\beta_0$ and $\beta=$, $(\beta_1, \ldots, \beta_d)$ are unknown regression intercept and coefficient parameters, respectively. Note that the prior probabilities can be also modeled using other regression models based on the SVs or the SSVs, such as linear regressions and non-linear regressions.

Based on (2), the posterior probability of the metabolite i being null is $$Pr(C_i=0 \mid z_i) = \frac{\pi_{i,0}f_0(z_i)}{f(z_i)} = 1 - \frac{\pi_{i,1}f_1(z_i)}{f(z_i)}$$

which we call the chemical structure-informed local false discovery rate (FDR). It ranges from 0 to 1. The smaller the value is for a metabolite, the higher the metabolite will be ranked as potential metabolomics signatures.

Two-sided tests are frequently used in discovery metabolomics studies. In such cases, the non-null metabolites can be further divided into two sub-states denoted as negative non-null and positive non-null. It is intuitive to distinguish the two non-null sub-states in the modeling. The indicator variable $C_i$ can takes three distinct values: $C_i=0$ for null, $C_i=1$ for negative non-null, and $C_i=2$ for positive non-null. The calculation of z-scores should also reflect the direction of the original test statistics. For instance, when two-sample t-tests are used to evaluate which metabolites are different between patients and controls, the z-scores can be defined as: $z_i=\text{sign}(t_i)\times\Phi^{-1}(1-p_i/2)$, where $t_i$ represents the t-statistic for the i-th metabolite. With this definition, either an extreme negative or extreme positive z-score indicates a departure from the null hypothesis. One can use a three-component RM model for the density of such z-scores:

$$f(z_i)=\pi_{i,0}f_0(z_i)+\pi_{i,1}f_1(z_i)+\pi_{i,2}f_2(z_i),$$

where the last two components correspond to the negative and positive non-null, respectively. Again the component density functions, $f_0$, $f_1$, and $f_2$, can be normal density or other types of density functions. When normal density functions (denoted by $\phi$) are used for the component density functions, the three-component RM model can be expressed as:

$$f(z_i)=\pi_{i,0}\phi(z_i;0,\sigma_0^2)+\pi_{i,1}\phi(z_i;\mu_1,\sigma_1^2)+\pi_{i,2}\phi(z_i;\mu_2^2).$$

where $\mu_1 < 0$ and $\mu_2 > 0$. Accordingly, we can estimate the log-ratios of prior probabilities between each non-null state and the null state with the SVs or the SSVs using the following link models:

$$\log=(\pi_{i,1}/\pi_{i,0})=\beta_{1,0}+\Sigma_{j=1}{}^{d}\beta_{1,j}D_{i,j},$$

$$\log=(\pi_{i,2}/\pi_{i,0})=\beta_{2,0}+\Sigma_{j=1}{}^{d}\beta_{2,j}D_{i,j}. \quad (3)$$

The chemical-structure-informed local FDRs for the i-th metabolite are: $1-\pi_{i,1}f_1(z_i)/f(z_i)$ for claiming it being negative non-null, and $1-\pi_{i,2}f_2(z_i)/f(z_i)$ for claiming it being positive non-null.

There are many other alternative ways to model the prior probabilities for the null and non-null states of the metabolites, e.g., the (generalized) proportional odds logit models. It is also worth mentioning that the number of components in the RM model can be extended to more than three.

As an optional step, one can further impose variable selection on the SVs or the SSVs to inform their relevance to the prior probabilities for the null and non-null states of metabolites. This can help indicate whether or not incorporating structure data of the metabolites into metabolomics data analysis will be helpful in a particular metabolomics study. Here we only elaborate this for the three-component RM model with a stochastic search variable selection (SSVS) method, and there are many other alternative methods for the task, such as adaptive shrinkage, reversible jump MCMC, and methods reviewed by OHara and Sillanpaa (*Bayesian Anal*, 4: 85-117, 2009).

Figure 2:
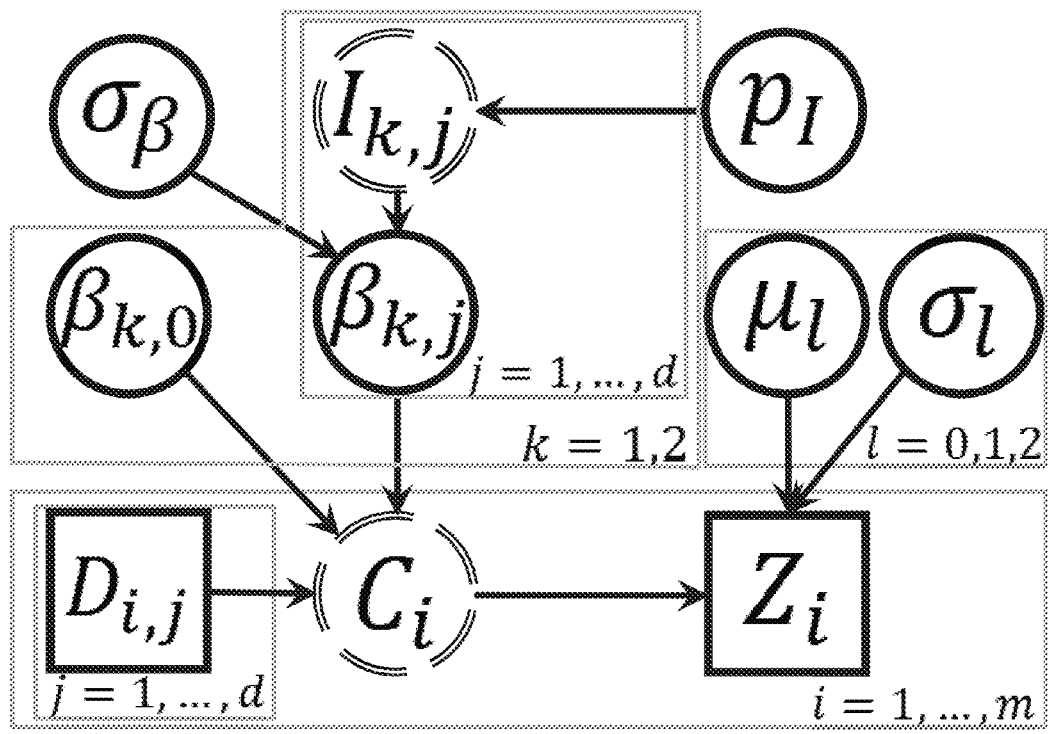
FIG. 2 illustrates the structure of a three-component regression mixture (RM) model. Circles indicate unknown parameters. Squares indicate observed input variables. Dashed circles are primary parameters of interest.

To implement SSVS, let $I_{k,j}$ be an indicator for the j-th SV or SSV being selected ($I_{k,j}=1$) or not ($I_{k,j}=0$) in the k-th Model in (3). The following mixture prior for $\beta_{k,j}$, k=1,2; j=1, . . . , d, can be used:

$$f(\beta_{k,j}|I_{k,j},\sigma_\beta^2)=(1-I_{k,j})\phi(\beta_{k,j};0,g\sigma_\beta^2)+I_{k,j}\phi(\beta_{k,j};0,\sigma_\beta^2),$$

where g is fixed to be a small positive number (e.g., 0.001). The following specification of the prior distributions for the unknown parameters in the model is just one specific example to implement SSVS among infinite numbers of other options: $\sigma_\beta \sim \text{Uniform}(0, 20)$; $I_{k,j}|p_I \sim \text{Bernoulli}(p_I)$; $p_I \sim \text{Uniform}(0,1)$; and $\beta_{k,0} \sim N(0, 10^2)$, for k=1,2. The prior distributions for the rest parameters in the RM model can be: $\mu_i \sim N(0, 10^6)I(a, 0)$, a truncated normal distribution between a=$\min_i z_i$ and 0; $\mu_2 \sim N(0, 10^6)I(0, b)$, b=$\max_i z_i$; and $\sigma_l^2 \sim \text{Inverse Gamma}(0.1, 0.1)$, for l=0,1,2. Similarly, there are infinite numbers of different choices for these prior distributions as well. One can also modify the prior specification for the regression coefficients in (3) to jointly select one SV or SSV in both link models, or to incorporate prior beliefs on the effects of SVs or SSVs. FIG. 2 shows a graphical representation of the structure of a three-component RM model.

The RM models can fitted with Markov chain Monte Carlo (MCMC) algorithms, which can be implemented using the software WinBUGS and run on the computer processors. As primary indices of interest, the posterior probabilities of a metabolite being in null/non-null states can be estimated from the MCMC sample mean of $C_i$'s, from which its corresponding chemical structure-informed local FDRs can be estimated as described above. Posterior inclusion probabilities of the SVs or the SSVs can be estimated from the MCMC sample mean of $I_{k,j}$'s. The inclusion probabilities for a SV or SSV ranging from 0 to 1 measure how often the SV or SSV is selected into the modeling of the prior probabilities for the states of metabolites, and thus reflect how much the input data favors the relevance of the SV or the SSV to the states of metabolites. Expectation maximization algorithms can be also used to fit the RM models.

Operation of the First Embodiment

To address a research question of interest in a metabolomics studying using the first embodiment of the invention, one collects metabolomics data by profiling a plurality of samples using one or several metabolomics devices. One can obtain chemical structures of the metabolites in the metabolomics data by searching chemical databases, and then calculate SVs for all the metabolites using one or several of the aforementioned methods or software. The structure data is then stored in storage medium. Optionally, the SVs can be further summarized into one or a plurality of SSVs using a dimension reduction method run on the computer processors. One then applies an appropriate routine statistical method programed to run on the computer processors to the metabolomics data with other necessary data, e.g., phenotype data, covariate data, etc., to derive original test statistics for the metabolites. A RM model run on the computer processors then takes the two sources of data, the SVs or the SSVs and the original test statistics, as inputs and generates chemical structure-informed FDRs for the metabolites and optionally posterior inclusion probabilities for the SVs or the SSVs. A metabolite with lower chemical structure-informed FDR is more likely to be a metabolomics signature.

Examplification of the First Embodiment

Metabolomics Study of Alzheimer's Disease

In this section, we further illustrate the first embodiment of the invention by applying it to a metabolomics study of Alzheimer's disease (AD). AD is a well-known neurodegenerative disorder and a leading cause of dementia with currently no effective cure or preventive therapy (http://www.alz.org). The goal of the study is to identify metabolites that have different levels between AD patients and cognitively normal (CN) participants, which may lead to new biomarkers and provide novel diagnostic and therapeutic insights. Therefore, the null hypothesis for a metabolite is that there is no difference in its level between AD and CN groups, denoted by 'AD=CN', while the positive non-null (negative non-null) is that its level is higher (lower) in the AD group than CN, denoted by 'AD>CN' ('AD<CN'). We profiled cerebrospinal fluid (CSF) samples from 40 AD and 38 CN subjects using two devices, a liquid-chromatography-electrochemical-array (LC-ECA) and a gas-chromatography-time-of-flight (GC-TOF) mass spectrometer. For each CSF sample, we identified and measured a total of 121 metabolites. We searched PubChem and KEGG to retrieve chemical structures of the metabolites, and then used the Dragon software run on a computer processor to calculate 882 SVs based on the chemical structures of the metabolites, which are all molecular descriptors (MD) including (but not limited to) ring descriptors, topological indices, walk and path counts, connectivity indices, and geometrical descriptors. SVs with zero variance for the metabolites were removed. One from each pair of highly correlated SVs (correlation coefficient≥0.95) was also removed. After these steps, 202 SVs remained. We then ran principal component analysis on the processor to summarize the SVs into five SSVs. We then analyzed the relative or absolute concentration levels of the metabolites using the following preprogrammed analyses on the processor to derive original test statistics for the metabolites: concentration levels of the metabolites were first adjusted for the use of two AD treatment drugs (binary variables) by building a linear regression model for each metabolite; then the residuals were compared between AD and CN subjects using Wilcoxon rank sum tests, which generated a p-value for each metabolite; and for each metabolite, a Hodges-Lehmann estimation of the difference in its concentration levels between AD and CN subjects was also calculated. A z-score was then calculated for each metabolite from its p-value and the Hodges-Lehmann estimation of the difference in its concentration levels between AD and CN subjects. We then run a pre-programed three-component RM model on the processor using the SSVs and the z-scores derived above so as to estimate chemical structure-informed local FDRs for each metabolites. For comparison purpose, we also applied a three-component standard normal mixture (SNM) model which is a widely-used conventional method that does not incorporate the structure data.

Figure 3:
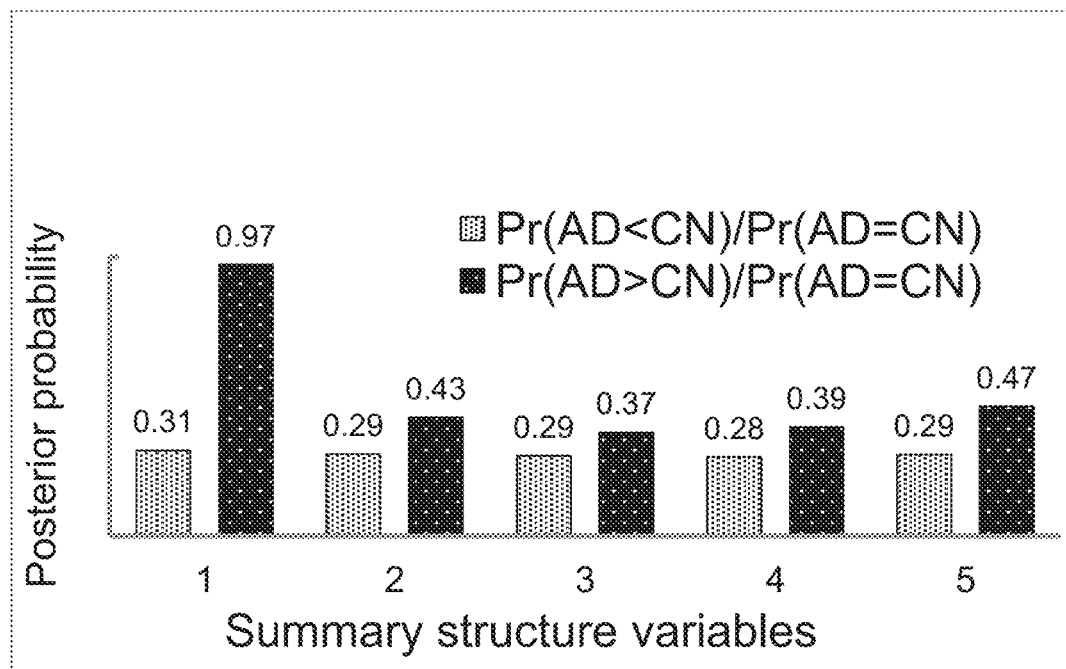
FIG. 3 shows the posterior inclusion probabilities for the SSVs estimated by the first embodiment of the invention applied to study Alzheimer's disease (AD).

Results show that the posterior inclusion probability for the first SSV in the modeling of the prior probability ratio between AD>CN and AD=CN reaches 0.97, and is much higher than those for the rest SSVs (FIG. 3). This suggests that the structure data is highly likely to be informative for the identification of metabolites that are increased in AD.

Table 1 provides analysis results for the metabolites that are given the lowest (≤0.05) chemical-structure-informed local FDR. These metabolites were ranked highest by the embodiment of the invention as potential AD metabolomics signatures. Compared to SNM, the conventional method, the embodiment of the invention promotes multiple metabolites that are actually mapped to two key neurotransmitter pathways: the purine and tryptophan metabolism pathways (FIG. 4). Also promoted are three carbohydrates, namely maltose, inulobiose, and sucrose, and pseudouridine. The following paragraphs of discussions show that these newly highlighted AD metabolomics signatures by the embodiment of the invention are well supported by existing knowledge on the molecular mechanisms of AD.

TABLE 1

Metabolomic differences between AD and CN participants that are given the lowest (≤0.05) chemical-structure-informed local FDR. Also provided are the local FDRs estimated by the SNM model not incorporating structure data.

| Metabolites | Non-null state | SNM-based Local FDR | Rank | Chemical-structure-informed Local FDR | Rank |
| --- | --- | --- | --- | --- | --- |
| Xanthosine | AD > CN | 0.11 | 1 | 0.00 | 1 |
| Inosine | AD > CN | 0.18 | 12 | 0.01 | 2 |
| 5-hydroxyindoleacetic acid | AD > CN | 0.17 | 10 | 0.01 | 3 |
| Guanosine | AD > CN | 0.36 | 32 | 0.02 | 4 |
| Vanillylmandelic acid | AD > CN | 0.14 | 6 | 0.02 | 5 |
| Indole-3-acetic acid | AD > CN | 0.19 | 13 | 0.02 | 6 |
| Glutathione | AD > CN | 0.11 | 2 | 0.03 | 7 |
| Kynurenine | AD > CN | 0.16 | 9 | 0.03 | 8 |
| Tryptophan | AD > CN | 0.35 | 31 | 0.03 | 9 |
| Sucrose | AD > CN | 0.29 | 23 | 0.04 | 10 |
| Inulobiose | AD > CN | 0.27 | 20 | 0.04 | 11 |
| Pseudouridine | AD > CN | 0.50 | 55 | 0.05 | 12 |
| Maltose | AD > CN | 0.51 | 56 | 0.05 | 13 |

Figure 4A:
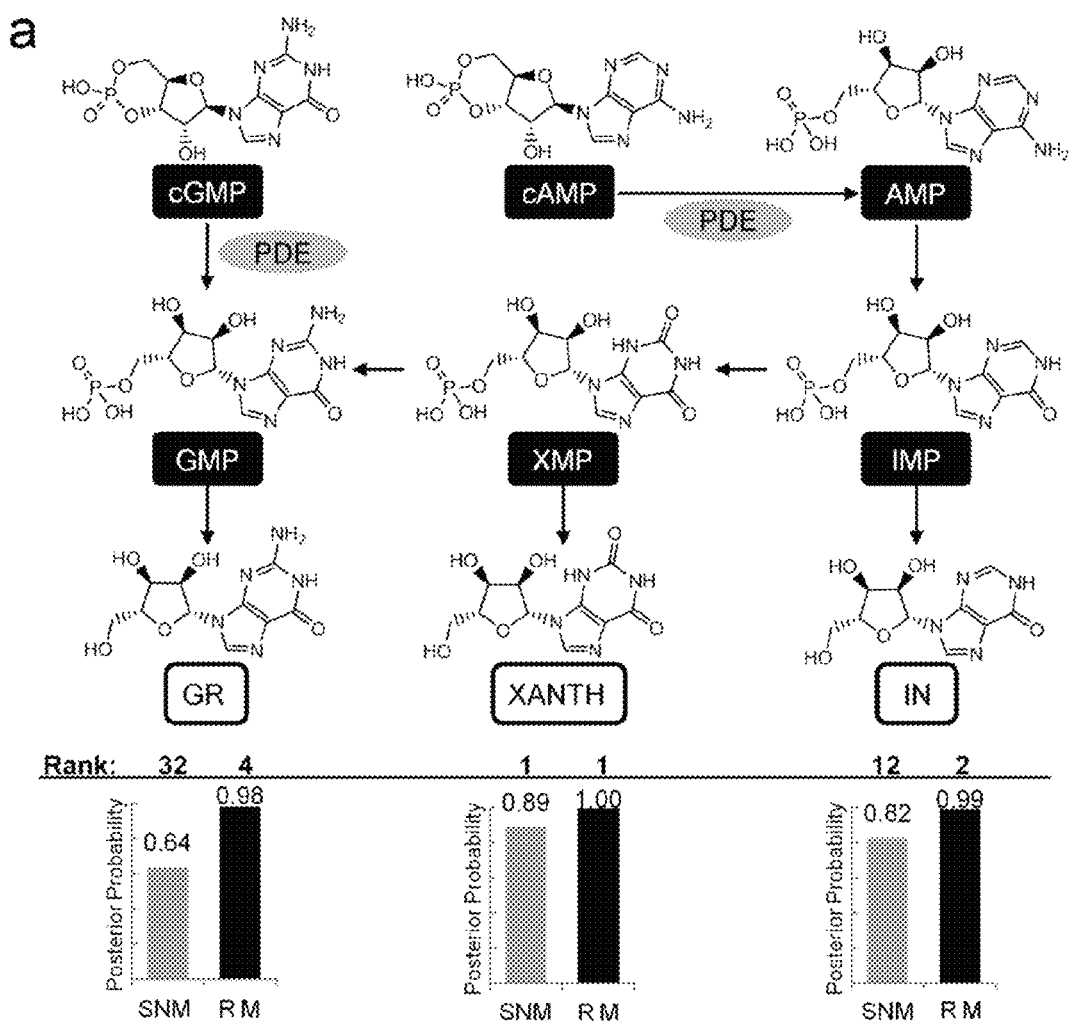
FIG. 4a shows metabolites on the purine metabolism pathways that were found elevated in AD patient by the first embodiment of the invention. Dark metabolites are not measured in the study. The bar plots give the posterior probabilities of the metabolites being higher in AD along with their ranks given by the first embodiment of the invention (denoted by RM in the figure) and a conventional method not incorporating structure data (denoted by SNM in the figure).

In the purine pathway (FIG. 4a), guanosine (GR) and inosine (IN) are highlighted by the embodiment of the invention, while xanthosine (XANTH) ranks highest by both the embodiment of the invention and the conventional method. As shown in FIG. 4a, cyclic adenosine monophosphate's (cAMP) and cyclic guanosine monophosphate (cGMP) are hydrolyzed by phosphodiesterases (PDE), whose expression and activity has been shown up-regulated in AD patients (Domek-Lopacinska and Strosznajder, *Mol Neurobiol*, 41: 129-37, 2010), leading to decreased cGMP and cAMP, and increased GR, IN, and XANTH. The decreased level of cGMP and cAMP, two important secondary messengers, is one of the key reasons for early AD symptoms, such as memory loss and poor judgment.

Figure 4B:
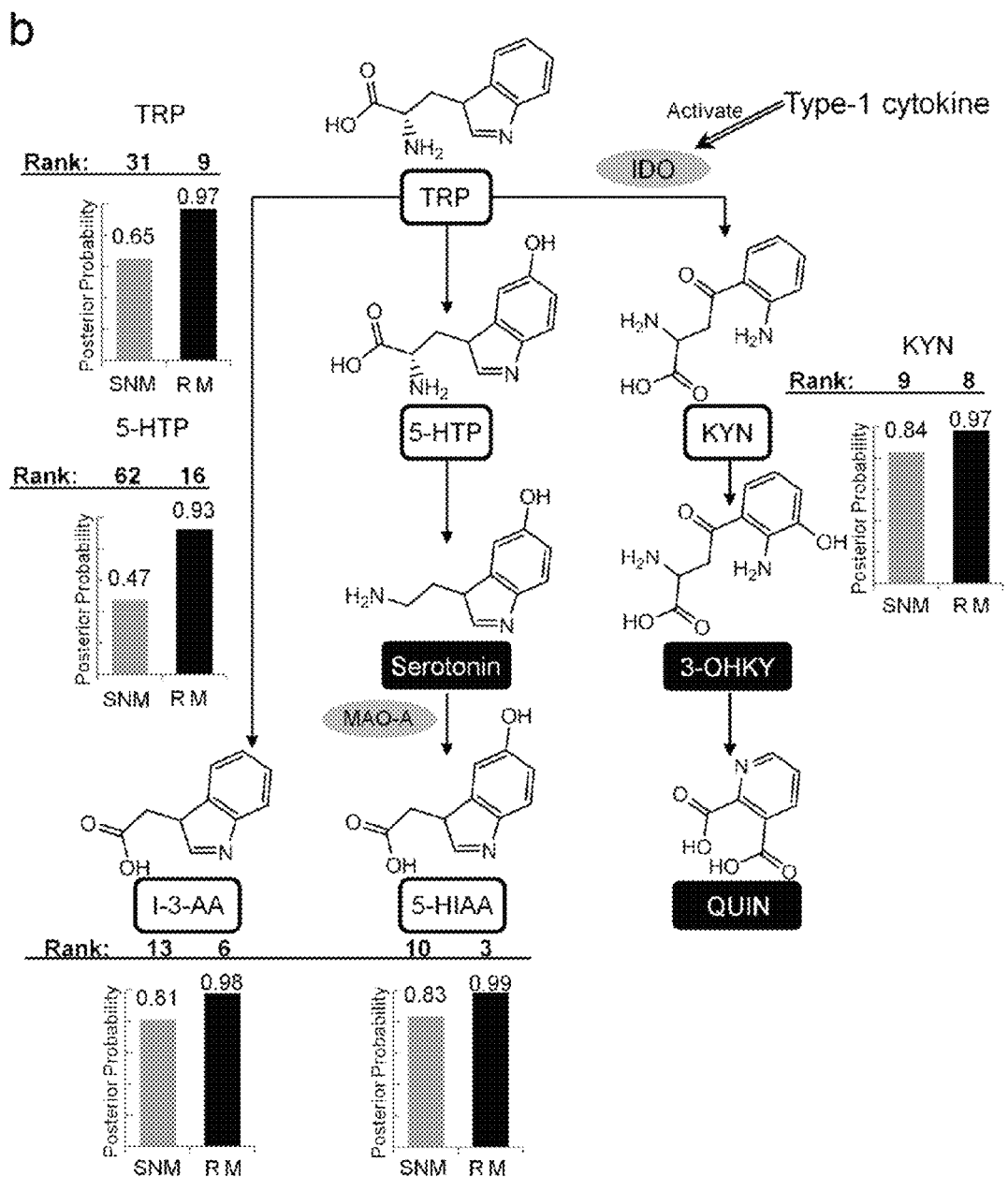
FIG. 4b shows metabolites on the tryptophan metabolism pathways that were found elevated in AD patient by the first embodiment of the invention. Dark metabolites are not measured in the study. The bar plots give the posterior probabilities of the metabolites being higher in AD along with their ranks given by the first embodiment of the invention (denoted by RM in the figure) and a conventional method not incorporating structure data (denoted by SNM in the figure).

The embodiment of the invention also identifies the abnormalities of tryptophan (TRP), 5-hydroxytryptophan (5-HTP), 5-hydroxyindoleacetic acid (5-HIAA), kynurenine (KYN), and indole-3-acetic acid (I-3-AA) in AD, which are all involved in the TRP metabolism pathway (FIG. 4b). The mechanism underlying the increased concentration of 5-HTP and 5-HIAA may involve the up-regulated monoamine oxidase-A (MAO-A) activity in AD, which has shown strong association with increased serotonin deamination (Kumagae et al., *Jpn J Pharmacol*, 55: 121-8, 1991), and thus the level of metabolites in the 5-HIAA branch. Recent studies show a markedly increased concentration of monocyte chemoattractant protein-1, a type 1 cytokine, in AD patients (Zhang et al., *J. Neuroimmunol.*, 256: 38-42, 2013), which induces indoleamine-pyrrole 2,3-dioxygenase (IDO) activation and thus up-regulates the catabolism of TRP into KYN, 3-hydroxykynurenine (3-OHKY), and quinolinic acid (QUIN). The increased level of I-3-AA may be another pathogenesis of AD due to its cytotoxic effect to neurons: the administration of I-3-AA in pregnant mice has been found to induce neuroepithelium apoptosis and decrease neuron formation in the fetuses (Furukawa et al., *Exp Toxicol Pathol*, 59, 43-52, 2007). Our findings provide further evidence for the involvement of the tryptophan pathway in elucidating the mechanisms of AD.

Maltose, inulobiose, and sucrose are a group of carbohydrates highlighted by the embodiment of the invention. Excess intake of these natural or artificial sweeteners has been shown in mouse models to cause insulin resistance and metabolic alterations (Cao et al., *J. Biol. Chem.*, 282: 36275-82, 2007; Carvalho et al., *Diabetes*, 61: 1234-42, 2012), which play important roles in the exacerbation of oxidative stress, mitochondrial abnormalities, and increased amyloid β protein levels in the brain. The correlation between high-carbohydrate diets and AD has been also reported in human studies (Henderson, *Med Hypotheses*, 62: 689-700, 2004).

Pseudouridine (Ψ) is the oxidized form of urinary nucleosides (Charette and Gray, *IUBMB Life*, 49: 341-51, 2000). Oxidative damage of RNA plays a critical role in the mechanisms of neurodegenerative disorders, including AD (Shan et al., *Faseb Journal*, 21: 2753-64, 2007). The potential mechanism of Ψ-induced brain damage might arise from the additional hydrogen bond in its structure compared with uridine, leading to increased risk of hydrogen bonding with the phosphate of its own or adjacent nucleotides. This structural change on RNA might cause an incorrect translation and thus decreased protein production and function in the brain. In addition, an increased level of pseudouridine in urine samples of AD patients has been reported recently (Lee et al., *Clin Biochem*, 40: 936-8. 2007).

CONCLUSION, RAMIFICATIONS, AND SCOPE

Accordingly the reader will see that at least one embodiment of the invented chemical structure-informed methods and systems for metabolomics data analysis can incorporate chemical structure information of metabolites into metabolomics data analysis process to improve the power of identifying metabolomics signatures. We also explained when describing the embodiment that the embodiment is applicable to many research questions in typical metabolomics studies, as long as these questions can be also answered by analyzing the relative or absolute concentration levels of the metabolites with or without other input data using some routine statistical tools. The advantages of the embodiment has been shown by an application of it to studying Alzheimer's disease, where it helps to identify new metabolomics signatures for the disease, which can help us better understand the underlying mechanisms of the disease and identify new molecular targets for further pharmaceutical development to treat the disease.

Although the above description contains much specificity, these should not be construed as limitations on the scope of any embodiment, but as exemplifications of various embodiments thereof. Many other ramifications and variations are possible, some of which have been given in the description of the first embodiment. To summarize a few of them, different methods and software can be used to calculate SVs for the metabolites;

different methods can be programed to run on the computer processors to summarize SVs into SSVs;

different statistical tools can be programed to run on the computer processors to derive the routine test statistics for the metabolites depending on what type of research question is to be addressed;

in addition to the RM model, other statistical tools can be programed to run on the computer processors to integrate the SVs or the SSVs with the routine test statistics to generate new test statistics for the metabolites;

in the RM model,
different density functions can be used;
more than three components can be included;
the prior probabilities of the metabolites being in different states can be also modeled using different regression models built on the SVs or the SSVs;
different variable selection methods can be used to select the SVs or the SSVs;
different prior distributions for the parameters in the model can be used;
expectation maximization (EM) algorithms can be used to fit the model.

Thus the scope of the embodiments should be determined by the appended claims and their legal equivalents, and not by the examples given.

We claim:

1. A method for analyzing metabolomics data using a storage medium for storing data and one or a plurality of computer processors for processing data and making calculations, comprising:
   a. retrieving chemical structures of said metabolites;
   b. converting said chemical structures of said metabolites into structure data of said metabolites including one or a plurality of structure variables;
   c. summarizing said structure variables into one or a plurality of summary structure variables;
   d. analyzing the relative or absolute concentration levels of said metabolites with or without other input data to derive one or a plurality of original test statistics for said metabolites; and
   e. integrating said structure variables or said summary structure variables with said original test statistics of said metabolites to derive new test statistics for said metabolites, whereby said structure data is incorporated to improve the evaluation of said metabolites in said metabolomics data.

2. The method of claim 1, wherein said retrieving chemical structures of said metabolites is searching the names or other identifications of said metabolites in a chemical database for chemical structures of said metabolites.

3. The method of claim 2, wherein said chemical database is cas, pubchem, chemspider, kegg, chembl, drug bank, or chebi.

4. The method of claim 1, wherein said structure variables are molecular descriptors, maccs key fingerprints, daylight, fingerprints, or other fingerprints.

5. The method of claim 4, wherein said molecular descriptors are calculated using adapt, admet predictor, adriana code, almond, bluedesc, cdk, codessa, comfa, dragon, e-dragon, grid, isida, joelib, marvin beans, moe, molconn-z, molgen-qspr, mold2, padel, powermv, or preadmet.

6. The method of claim 1, wherein said summarizing said structure variables into one or a plurality of summary structure variables is applying a dimension reduction method.

7. The method of claim 6, wherein said dimension reduction method is principal component analysis, a variation of principal component analysis, kernel principal component analysis, factor analysis, a variation of factor analysis, singular value decomposition, isomap, a variation of isomap, multidimensional scaling, or a variation of multidimensional scaling.

8. The method of claim 1, wherein said summarizing said structure variables into one or a plurality of summary structure variables is directly using said structure variables as said summary structure variables.

9. The method of claim 1, wherein said other input data includes one or more of the following: phenotype data, covariate data, and sampling time data.

10. The method of claim 1, wherein said analyzing the relative or absolute concentration levels of said metabolites with or without other input data to derive one or a plurality of original test statistics for said metabolites is using a linear regression analysis, a nonlinear regression analysis, a t-test, a parametric test or a non-parametric test to analyze the relative or absolute concentration levels of said metabolites with or without said other input data.

11. The method of claim 1, wherein said new test statistics are false discovery rates.

12. The method of claim 1, further including evaluating the relevance of said structure data.

13. The method of claim 1, wherein said integrating said structure variables or said summary structure variables with said original test statistics of said metabolites to derive new test statistics for said metabolites is building a mixture model consisting of a plurality of components, each of said components comprising a prior probability and a component distribution, for modeling the distribution of said original test statistics for said metabolites.

14. The method of claim 13, wherein said mixture model uses said structure variables or said summary structure variables of said metabolites to model the prior probabilities.

* * * * *